United States Patent [19]

Stach

[11] 4,319,914

[45] Mar. 16, 1982

[54] HERBICIDAL TETRAHYDROBENZOTHIAZOLYLIMIDAZOLIDINONES

[75] Inventor: Leonard J. Stach, Riverside, Ill.

[73] Assignee: Velsicol Chemical Corporation, Chicago, Ill.

[21] Appl. No.: 129,064

[22] Filed: Mar. 10, 1980

Related U.S. Application Data

[63] Continuation-in-part of Ser. No. 16,854, Mar. 2, 1979, abandoned.

[51] Int. Cl.³ .................... A01N 43/54; C07D 277/60
[52] U.S. Cl. ........................................ 71/90; 548/162
[58] Field of Search .................... 71/90; 260/306.8 F; 548/162

[56] References Cited

U.S. PATENT DOCUMENTS

| | | | |
|---|---|---|---|
| 3,682,945 | 8/1972 | Engelhart | 260/306.8 F |
| 3,780,051 | 12/1973 | Litt et al. | 260/306.8 F |
| 3,901,904 | 8/1975 | Krenzer | 260/306.8 D |
| 4,029,491 | 6/1977 | Krenzer et al. | 71/90 |
| 4,086,241 | 4/1978 | Wu et al. | 260/306.8 D |

*Primary Examiner*—Catherine L. Mills
*Attorney, Agent, or Firm*—Dietmar Olesch; Robert J. Schwarz

[57] ABSTRACT

This invention discloses a compound of the formula

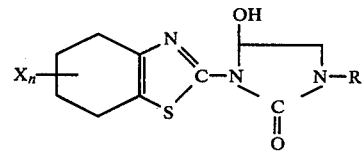

wherein X is selected from the group consisting of alkyl, halogen, and cyano; n is an integer from 0 to 4; and R is selected from the group consisting of alkyl, alkenyl and haloalkyl.

The foregoing compounds are useful as herbicides.

5 Claims, No Drawings

HERBICIDAL TETRAHYDROBENZO-THIAZOLYLIMIDAZOLIDINONES

This application is a continuation-in-part application of my copending application Ser. No. 16,854 filed Mar. 2, 1979, now abandoned.

This invention relates to new compositions of matter. More specifically, this invention relates to new chemical compounds of the formula:

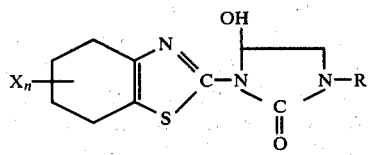

wherein X is selected from the group consisting of hydrogen alkyl, halogen, and cyano; n is an integer from 0 to 4; and R is selected from the group consisting of alkyl, alkenyl, haloalkyl and alkynyl.

The compounds of the present invention are unexpectedly useful as herbicides and are particularly effective in the post-emergence control of weeds.

In an preferred embodiment of this invention X is selected from the group consisting of lower alkyl, chlorine, bromine, and cyano; and R is selected from the group consisting of lower alkyl, lower alkenyl, lower chloroalkyl and propargyl.

The compounds of the present invention can be readily prepared by heating a compound of the formula

wherein X, n and R are as heretofore described, in a dilute, aqueous, acidic reaction medium for a period of about 10 to about 90 minutes. Temperatures of from about 60° C. to the reflux temperature of the reaction mixture can be utilized. The reaction medium can comprise a dilute aqueous inorganic acid such as hydrochloric acid at a concentration of from about 0.5 to about 5 percent. Acidic water-ethanol mixtures can also be used. Upon completion of the reaction, the desired product can be recovered as a precipitate or residue upon cooling or evaporation of the reaction mixture. This product can be used as such or can be further purified by conventional means such as recrystallization and the like.

The compounds of Formula II can be prepared by reacting a carbamate of the formula

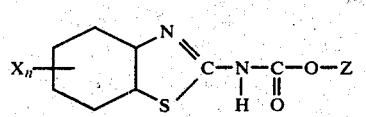

wherein Z is methyl or ethyl, and X and n are as heretofore described, with an acetal of the formula

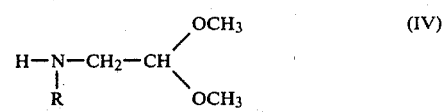

wherein R is as heretofore described. This reaction can be effected by dissolving the compound of Formula III in an equimolar or slight molar excess of the acetal of Formula IV and heating the resulting mixture at a temperature of from about 90° C. to about 130° C. for a period of from 12 to 48 hours in a reaction vessel blanketed with inert gas. The reaction product can then be recovered upon distillation to remove unreacted starting material and can be used as such or can be further purified if desired by standard techniques.

The compounds of Formula III are known in the literature but when not readily available can be prepared from a compound of the formula

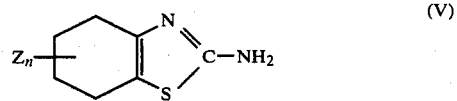

wherein Z and n are as heretofore described, by reaction with methyl or ethyl chloroformate. This reaction can be effected by slowly adding the chloroformate to a solution of the compound of Formula III in an organic solvent in the presence of an acid acceptor. The acid acceptor itself may serve as the solvent such as for example pyridine. After the addition is completed, stirring of the reaction mixture can be continued to ensure completion of the reaction. After such time the desired product can be recovered and can be purified by conventional techniques such washing to remove acid acceptor hydrochloride, recrystallization and the like.

The compounds of Formula V when not readily available can be prepared by the techniques referred to in U.S. Pat. No. 3,682,945.

The compounds of Formula II can also be prepared by reacting a molar amount of an isocyanate dimer of the formula

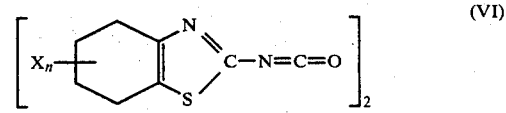

wherein X and n are as heretofore described, with about two molar amounts of a dimethyl acetal of the formula

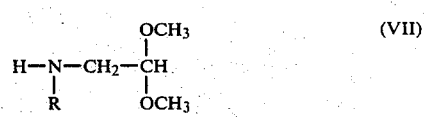

wherein $R^2$ is as heretofore described. This reaction can be effected by heating a mixture of the isocyanate dimer and the acetal in an inert organic reaction medium such as toluene at the reflux temperature of the reaction mixture. Heating at reflux can be continued for a period of from about 2 to about 30 minutes to ensure completion of the reaction. After this time the desired product can be recovered upon evaporation of the reaction medium and can be used as such or can be further purified by standard techniques in the art.

The isocyanate dimer of Formula VI can be prepared by reacting the tetrahydrobenzothiazole of Formula V with phosgene. This reaction can be effected by adding a slurry or solution of the benzothiazole, in a suitable organic solvent such as ethyl acetate, to a saturated solution of phosgene in an organic solvent such as ethyl acetate. The resulting mixture can be stirred at ambient temperatures for a period of from about 4 to about 24 hours. The reaction mixture can then be purged with nitrogen gas to remove unreacted phosgene. The desired product can then be recovered by filtration, if formed as a precipitate, or upon evaporation of the organic solvent used if soluble therein. This product can be used as such or can be further purified as desired.

Exemplary tetrahydrobenzothiazole compounds of Formula V suitable for preparing the compounds of the present invention are:
2-amino-4,5,6,7-tetrahydrobenzothiazole
2-amino-4-chloro-4,5,6,7-tetrahydrobenzothiazole
2-amino-5-methyl-4,5,6,7-tetrahydrobenzothiazole
2-amino-7-ethyl-4,5,6,7-tetrahydrobenzothiazole
2-amino-5-hexyl-4,5,6,7-tetrahydrobenzothiazole
2-amino-5-cyano-4,5,6,7-tetrahydrobenzothiazole
2-amino-5,5-diethyl-4,5,6,7-tetrahydrobenzothiazole
2-amino-5-methyl-7-propoxy-4,5,6,7-tetrahydrobenzothiazole Exemplary suitable acetals of Formula IV for preparing the compounds of this invention are the dimethyl acetal of 2-methylaminoacetaldehyde, the dimethyl acetal of 2-ethylaminoacetaldehyde, the dimethyl acetal of 2-propylaminoacetaldehyde, the dimethyl acetal of 2-butylaminoacetaldehyde, the dimethyl acetal of 2-pentylaminoacetaldehyde and the dimethyl acetal of 2-hexylaminoacetaldehyde.

The manner in which the compounds of the present invention can be prepared is more specifically illustrated in the following examples.

EXAMPLE 1

Preparation of 2-Amino-5,5,7,7-tetramethyl-4,5,6,7-tetrahydrobenzothiazole 3,3,5,5-Tetramethylcyclohexanone (9.9 grams), cyanamid (2.1 grams), sulfur (1.6 grams) and ethanol (8 ml) were charged into a glass reaction vessel equipped with a mechanical stirrer and addition funnel. Diethylamine (5 ml) was then added dropwise to the reaction mixture with cooling to maintain the reaction mixture below about 45° C. After the addition was completed, the reaction mixture was heated at 40° to 45° C. for a period of 2 hours. After this time the reaction mixture was poured into water (100 ml) and was acidified with hydrochloric acid to a pH of 4. The mixture was then washed with ether and the aqueous phase withdrawn and adjusted to a pH of 9 with aqueous sodium hydroxide. The resulting mixture was extracted with ether. The ether extract was then dried over anhydrous magnesium sulfate and evaporated to yield the desired product 2-amino-5,5,7,7-tetramethyl-4,5,6,7-tetrahydrobenzothiazole as a solid melting at 120° to 122°.

EXAMPLE 2

Preparation of Ethyl N-(5,5,7,7-Tetramethyl-4,5,6,7-tetrahydrobenzothiazol-2-yl)carbamate 2-Amino-5,5,7,7-tetramethyl-4,5,6,7-tetrahydrobenzothiazole (16 grams; 0.075 mol) dissolved in pyridine (100 ml) was charged into a glass reaction vessel equipped with a mechanical stirrer and addition funnel. Ethyl chloroformate (11 grams; 0.1 mol) was then added dropwise with stirring and cooling of the reaction mixture. After the addition was completed the reaction mixture was allowed to warm to room temperature and stirring was continued for a period of about 1 hour. After this time the reaction mixture was poured into ice water resulting in a white precipitate. The precipitate was recovered by filtration, was dried and recrystallized from methanol to yield the desired product ethyl N-(5,5,7,7-tetramethyl-4,5,6,7-tetrahydrobenzothiazol-2-yl) carbamate having a melt point of 124° to 125° C.

EXAMPLE 3

Preparation of the Dimethyl Acetal of 2-[1-Methyl-3-(5,5,7,7-tetramethyl-4,5,6,7-tetrahydrobenzothiazol-2-yl)ureido]acetaldehyde Ethyl N-(5,5,7,7-tetramethyl-4,5,6,7-tetrahydrobenzothiazol-2-yl)carbamate (2 grams) and the dimethyl acetal of 2-methyl-aminoacetaldehyde (20 ml) were charged into a glass reaction flask equipped with a magnetic stirrer, reflux condenser and gas addition tube. The reaction mixture was blanketed with nitrogen gas and was heated at 120° C. for a period of about 50 hours. After this time the reaction mixture was distilled under reduced pressure to remove excess unreacted starting material leaving a brown oily residue. This residue was purified by elution chromotography using ethyl acetate as the eluant. The chromatographed solution was then stripped of solvent to yield the desired product dimethyl acetal of 2-[1-methyl-3-(5,5,7,7-tetramethyl-4,5,6,7-tetrahydrobenzothiazol-2-yl)ureido]acetaldehyde as a colorless solid having a melting point of 108° C.

EXAMPLE 4

Preparation of 1-(5,5,7,7-Tetramethyl-4,5,6,7-tetrahydrobenzothiazol-2-yl)-3-methyl-5-hydroxy-1,3-imidazolidin-2-one The dimethyl acetal of 2-[1-methyl-3-(5,5,7,7-tetramethyl-4,5,6,7-tetrahydrobenzothiazol-2-yl)ureido]acetaldehyde (2.5 grams) was dissolved in dilute hydrochloric acid (25 ml; 3.7% conc.). The solution was heated at a temperature of 85° C. for a period of about 10 minutes resulting in the formation of a precipitate. Additional hydrochloric acid (15 ml) was added and stirring was continued for about 90 minutes. After this time the precipitate was recovered by filtration, was washed with water and dried to yield the desired product 1-(5,5,7,7-tetramethyl-4,5,6,7-tetrahydrobenzothiazol-2-yl)-3-methyl-5-hydroxy-1,3-imidazolidin-2-one having a melt point of 135° to 138° C.

EXAMPLE 5

Preparation of 5,5,7-Trimethyl-4,5,6,7-tetrahydrobenzothiazol-2-yl Isocyanate Dimer A saturated solution of phosgene in ethyl acetate (200 ml) and 2-amino-5,5,7-trimethyl-4,5,6,7-tetrahydrobenzothiazole (6.0 grams) were charged into a glass reaction vessel equipped with a mechanical stirrer and reflux condenser. The reaction mixture was heated at reflux for a period of about 5 hours. After this time the reaction was stripped of solvent and unreacted starting materials to yield the desired product 5,5,7-trimethyl-4,5,6,7-tetrahydrobenzothiazol-2-yl-isocyanate dimer as a brown crystalline solid.

EXAMPLE 6

Preparation of the Dimethyl Acetal of 2-[1-Methyl-3-(5,5,7-trimethyl-4,5,6,7-tetrahydrobenzothiazol-2-yl)-ureido]acetaldehyde 5,5,7-Trimethyl-4,5,6,7-tetrahydrobenzothiazol-2-yl isocyanate dimer (7.5 grams), the dimethyl acetal of 2-methyl-aminoacetaldehyde (5 grams) and toluene (15 ml) were charged into a glass reaction vessel equipped with a mechanical stirrer and reflux condenser. The reaction mixture was then heated, with stirring for a period of about 1 hour. After this time the mixture was cooled and filtered. The filtrate was washed with water, dried and evaporated, leaving the desired product dimethyl acetal of 2-[1-methyl-3-(5,5,7-trimethyl-4,5,6,7-tetrahydrobenzothiazol-2-yl)ureido]acetaldehyde as a brown oil.

EXAMPLE 7

Preparation of 1-(5,5,7-Trimethyl-4,5,6,7-tetrahydrobenzothiazol-2-yl)-3-methyl-5-hydroxy-1,3-imidazolidin-2-one The dimethyl acetal of 2-[1-methyl-3-(5,5,7-trimethyl-4,5,6,7-tetrahydrobenzothiazol-2-yl)ureido]acetaldehyde (8.5 grams), water (25 ml), ethanol (25 ml) and concentrated hydrochloric acid (8.5 ml) were charged into a glass reaction vessel equipped with a mechanical stirrer, thermometer and reflux condenser. The reaction mixture was then heated at reflux for a period of about 10 minutes. After this time the reaction mixture was stripped of solvents to yield the desired product 1-(5,5,7-trimethyl-4,5,6,7-tetrahydrobenzothiazol-2-yl)-3-methyl-5-hydroxy-1,3-imidazolidin-2-one as a brown solid.

EXAMPLE 8

Preparation of Ethyl N-(5-Ethyl-7-chloro-4,5,6,7-tetrahydrobenzothiazol-2-yl)carbamate 2-Amino-5-ethyl-7-chloro-4,5,6,7-tetrahydrobenzothiazole (0.10 mol) dissolved in pyridine (125 ml.) is charged into a glass reaction vessel equipped with a mechanical stirrer, thermometer and addition funnel. Ethyl chloroformate (0.12 mol) is then added dropwise to the reaction mixture with stirring and cooling. After the addition is completed the reaction mixture is allowed to warm to room temperature and stirring is continued for a period of about 1 hour. After this time the reaction mixture is poured into ice water to form a precipitate. The precipitate is recovered by filtration, is dried and recrystallized to yield the desired product ethyl N-(5-ethyl-7-chloro-4,5,6,7-tetrahydrobenzothiazol-2-yl)carbamate.

EXAMPLE 9

Preparation of the Dimethyl Acetal of 2-[1-Allyl-3-(5-ethyl-7-chloro-4,5,6,7-tetrahydrobenzothiazol-2-yl)-ureido]acetaldehyde Ethyl N-(5-ethyl-7-chloro-4,5,6,7-tetrahydrobenzothiazol-2-yl)-carbamate (0.08 mol) and the dimethyl acetal of 2-allylaminoacetaldehyde (30 ml.) are charged into a glass reaction vessel equipped with a stirrer, reflux condenser and gas addition tube. The reaction mixture is blanketed with nitrogen gas and is heated at 125° C. for a period of about 8 hours. After this time the reaction mixture is distilled to remove excess starting material. The residue is purified by elution chromatography using ethyl acetate as the eluant. The chromatographed solution is then stripped of solvent to yield the desired product dimethyl acetal of 2-[1-allyl-3-(5-ethyl-7-chloro-4,5,6,7-tetrahydrobenzothiazol-2-yl)ureido]acetaldehyde.

EXAMPLE 10

Preparation of 1-(5-Ethyl-7-chloro-4,5,6,7-tetrahydrobenzothiazol-2-yl)-3-allyl-5-hydroxy-1,3-imidazolidin-2-one The dimethyl acetal of 2-[1-allyl-3-(5,5-diethyl-4,5,6,7-tetrahydrobenzothiazol-2-yl)ureido]acetaldehyde (0.05 mol) and dilute hydrochloric acid (25 ml; 3% conc.) are charged into a glass reaction vessel equipped with a mechanical stirrer and thermometer. The reaction mixture is heated at a temperature of about 85° C. for a period of about 45 minutes resulting in the formation of a precipitate. After this time the precipitate is recovered by filtration and dried to yield the desired product 1-(5-ethyl-7-chloro-4,5,6,7-tetrahydrobenzothiazol-2-yl)-3-allyl-5-hydroxy-1,3-imidazolidin-2-one.

EXAMPLE 11

Preparation of Ethyl N-(5-Propyl-7-cyano-4,5,6,7-tetrahydrobenzothiazol-2-yl)carbamate 2-Amino-5-propyl-7-cyano-4,5,6,7-tetrahydrobenzothiazole (0.10 mol) dissolved in pyridine (125 ml.) is charged into a glass reaction vessel equipped with a mechanical stirrer, thermometer and addition funnel. Ethyl chloroformate (0.12 mol) is then added dropwise to the reaction mixture with stirring and cooling. After the addition is completed the reaction mixture is allowed to warm to room temperature and stirring is continued for a period of about 1 hour. After this time the reaction mixture is poured into ice water to form a precipitate. The precipitate is recovered by filtration, is dried and recrystallized to yield the desired product ethyl-N-(5-propyl-7-cyano-4,5,6,7-tetrahydrobenzothiazol-2-yl)carbamate.

EXAMPLE 12

Preparation of the Dimethyl Acetal of 2-[1-But-3-enyl-3-(5-propyl-7-cyano-4,5,6,7-tetrahydrobenzothiazol-2-yl)-ureido]acetaldehyde Ethyl N-(5-propyl-7-cyano-4,5,6,7-tetrahydrobenzothiazol-2-yl)carbamate (0.08 mol) and the dimethyl acetal of 2-but-3-enylaminoacetaldehyde (30 ml.) as charged into a glass reaction vessel equipped with a stirrer, reflux condenser and gas addition tube. The reaction mixture is blanketed with nitrogen gas and is heated 125° C. for a period of about 8 hours. After this time the reaction mixture is distilled to remove excess starting material. The residue is purified by elution chromatography using ethyl acetate as the eluant. The chromatographed solution is then stripped of solvent to yield the desired product dimethyl acetal of 2-[1-but-3-enyl-3-(5-propyl-7-cyano-4,5,6,7-tetrahydrobenzothiazol-2-yl)ureido]acetaldehyde.

EXAMPLE 13

Preparation of 1-(5-Propyl-7-cyano-4,5,6,7-tetrahydrobenzothiazol-2-yl)-3-but-3-enyl-5-hydroxy-1,3-imidazolidin-2-one The dimethyl acetal of 2-[1-but-3-enyl-3-(5-propyl-7-cyano-4,5,6,7-tetrahydrobenzothiazol-2-yl)ureido]acetaldehyde (0.05 mol) and dilute hydrochloric acid (25 ml; 3% conc.) are charged into a glass reaction vessel equipped with a mechanical stirrer and thermometer. The reaction mixture is heated at a temperature of about 85° C. for a period of about 45 minutes resulting in the formation of a precipitate. After this time the precipitate is recovered by filtration and dried to yield the desired product 1-(5-propyl-7-cyano-4,5,6,7-tetrahydrobenzothiazol-2-yl)-3-but-3-enyl-5-hydroxy-1,3-imidazolidin-2-one.

EXAMPLE 14

Preparation of 2-Amino-4,5,6,7-tetrahydrobenzothiazole 2-chlorocyclohexanone (6.63 grams; 0.05 mol) and thiourea (3.81 grams; 0.05 mol) were charged into a glass reaction vessel and heated overnight on a steam bath. The product was poured in water (100 ml.) and was acidified with hydrochloric acid. The unreacted ketone was extracted from the reaction mixture by using ethanol (25 ml.) five times and the aqueous portion withdrawn and adjusted to a pH of 9 with aqueous sodium hydroxide. The product was then extracted with ethanol, dried over anhydrous magnesium sulfate and evaporated on a rotary evaporator resulting in 6.3 grams of desired product having a melting point of 84°-87° C. The structure of the product was confirmed by infrared spectroscopy.

EXAMPLE 15

Preparation of Ethyl N-(4,5,6,7-Tetrahydrobenzothiazol-2-yl)carbamate

2-Amino-4,5,6,7-tetrahydrobenzothiazole (12.3 grams; 0.08 mol) dissolved in pyridine (50 ml.) was charged into a glass reaction vessel equipped with a mechanical stirrer, thermometer and addition funnel. Ethyl chloroformate (12 ml; 0.11 mol) was added dropwise to the reaction mixture with stirring and cooling. After the addition was completed the reaction mixture was allowed to warm to room temperature and stirring was continued for a period of about 1 hour. After this time the reaction mixture was poured into ice water (50 mol.) to form a precipitate. The precipitate was recovered by filtration, washed with water four times dried and recrystallized from ethanol to yield the desired product ethyl N-(4,5,6,7-tetrahydrobenzothiazol-2-yl)carbamate; (16.7 grams); melting point 182°-184° C. The structure of the product was verified by infrared and NMR spectroscopy.

EXAMPLE 16

Preparation of the Dimethyl Acetal of 2-[1-Methyl-3-(4,5,6,7-tetrahydrobenzothiazol-2-yl)ureido]-acetaldehyde Ethyl N-(4,5,6,7-tetrahydrobenzothiazol-2-yl)carbamate (13.6 grams; 0.06 mol) and the dimethyl acetal of 2-methylaminoacetaldehyde (20 mol.) were charged into a glass reaction vessel equipped with a stirrer, reflux condenser and gas addition tube. The reaction mixture was blanketed with nitrogen gas and heated at 120° C. for a period of 24 hours. Since starting material remained, the mixture was heated for an additional 48 hours and then for an additional 18 hours. After this time the reaction mixture was distilled to remove excess starting material. The residue was purified by chromatography using ethyl acetate as the eluant on silica gel adsorbant yielding the desired product, dimethyl acetal of 2-[1-methyl-3-(4,5,6,7-tetrahydrobenzothiazol-2-yl)ureido]acetaldehyde; (8.9; melting point 89°-92° C.). The structure of the product was verified by infrared and NMR spectroscopy.

EXAMPLE 17

Preparation of 1-(4,5,6,7-tetrahydrobenzothiazol-2-yl)-3 methyl-5-hydroxy-1,3-imidazolidin-2-one The dimethyl acetal of 2-[1-methyl-3-(4,5,6,7-tetrahydrobenzothiazol-2-yl)ureido]acetaldehyde (2.99 grams) and dilute hydrochloric acid (40 ml; 3.7% conc.) are charged into a glass reaction vessel equipped with a mechanical stirrer and thermometer. The reaction mixture is heated at a temperature of about 85° C. for a period of about 20 minutes resulting in the formation of a precipitate. The solution was neutralized with sodium bicarbonate, the precipitate filtered, washed with water and dried yielding the desired product, 1-(4,5,6,7-tetrahydrobenzothiazol-2-yl)-3-methyl-5-hydroxy-1,3-imidazolidin-2-one, (2.2 grams), melting point 174°-176° C. The structure of the product was verified by infrared and NMR spectroscopy.

| Elemental analysis: | C | H | N |
|---|---|---|---|
| Theoretical | 52.15 | 5.97 | 16.59 |
| Found | 52.13 | 6.08 | 16.49 |

Additional compounds within the scope of the present invention which can be prepared by the methods detailed in the foregoing examples are:
1-(5,7-dibutyl-4,5,6,7-tetrahydrothiazol-2-yl)-3-β-fluoroethyl-5-hydroxy-1,3-imidazolidin-2-one, 1-(5,5,7-triethyl-4,5,6,7-tetrahydrothiazol-2-yl)-3-δ-chlorohexyl-5-hydroxy-1,3-imidazolidin-2-one, 1-)5,5,7-trimethyl-7-cyano-4,5,6,7-tetrahydrothiazol-2-yl)-3-methyl-5-hydroxy-1,3-imidazolidin-2-one, 1-(5-cyano-5,7-dimethyl-4,5,6,7-tetrahydrothiazol-2-yl)-3-methyl-5-hydroxy-1,3-imidazolidin-2-one, 1-(5-dimethylamino-4,5,6,7-tetrahydrothiazol-2-yl)3-methyl-5-hydroxy-1,3-imidazolidin-2-one, 1-(5-diethylamino-4,5,6,7-tetrahydrothiazol-2-yl)-3-methyl-5-hydroxy-1,3-imidazolidin-2-one, 1-(7-dibutylamino-4,5,6,7-tetrahydrothiazol-2-yl)-3-propargyl-5-hydroxy-1,3-imidazolidin-2-one, 1-(5,5,7-trimethyl-4,5,6,7-tetrahydrothiazol-2-yl)-3-propargyl-5-hydroxy-1,3-imidazolidin-2-one, 1-(5-bromo-4,5,6,7-tetrahydrothiazol-2-yl)-3-propargyl-5-hydroxy-1,3-imidazolidin-2-one.

For practical use as herbicides the compounds of this invention are generally incorporated into herbicidal compositions which comprise an inert carrier and a herbicidally toxic amount of such a compound. Such herbicidal compositions, which can also be called formulations, enable the active compound to be applied conveniently to the site of the weed infestation in any desired quantity. These compositions can be solids such as dusts, granules, or wettable powders; or they can be liquids such as solutions, aerosols or emulsifiable concentrates.

For example, dusts can be prepared by grinding and blending the active compound with a solid inert carrier such as the talcs, clays, silicas, pyrophyllite, and the like. Granular formulations can be prepared by impregnating the compound, usually dissolved in a suitable solvent, onto and into granulated carreiers such as the attapulgites or the vermiculites, usually of a particle size range of from about 0.3 to 1.5 mm. Wettable powders, which can be dispersed in water or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of herbicides can be dispersed under super-atmospheric pressure as aerosols. However, preferred liquid herbicidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the weed infestation. The emulsifiers most commonly used in these concentrates are nonionic or mixtures of nonionic with anionic surface-active agents. With the use of some emulsifier systems an inverted emulsion (water in oil) can be prepared for direct application to weed infestations.

A typical herbicidal composition according to this invention is illustrated by the following example, in which the quantities are in parts by weight.

EXAMPLE 18

Preparation of a Dust

Product of Example 4: 10
Powdered Talc: 90

The above ingredients are mixed in a mechanical grinder-blender and are ground until a homogeneous, free-flowing dust of the desired particle size is obtained. This dust is suitable for direct application to the site of the weed infestation.

The compounds of this invention can be applied as herbicides in any manner recognized by the art. One method for the control of weeds comprises contacting the locus of said weeds with a herbicidal composition comprising an inert carrier and as an essential active ingredient, in a quantity which is herbicidally toxic to said weeds, a compound of the present invention. The concentration of the new compounds of this invention in the herbicidal compositions will vary greatly with the type of formulation and the purpose for which it is designed, but generally the herbicidal compositions will comprise from about 0.05 to about 95 percent by weight of the active compounds of this invention. In a preferred embodiment of this invention, the herbicidal compositions will comprise from about 5 to about 75 percent by weight of the active compound. The compositions can also comprise such additional substances as other pesticides, such as insecticides, nematocides, fungicides, and the like; stabilizers, spreaders, deactivators, adhesives, stickers, fertilizers, activators, synergists and the like.

The compound of the present invention are also useful when combined with other herbicides and/or defoliants, dessicants, growth inhibitors and the like in the herbicidal compositions heretofore described. These other materials can comprise from about 5% to about 95% of the active ingredients in the herbicidal compositions. Use of combinations of these other herbicides and/or defoliants, dessicants, etc. with the compounds of the present invention provide herbicidal compositions which are more effective in controlling weeds and often provide results unattainable with separate compositions of the individual herbicides. The other herbicides, defoliants, dessicants and plant growth inhibitors, with which the compounds of this invention can be used in the herbicidal compositions to control weeds, can include chlorophenoxy herbicides such as 2,4-D, 2,4,5-T, MCPA, MCPB, 4(2,4-DB), 2,4-DEB, 4-CPB, 4-CPA, 4-CPP, 2,4,5-TB, 2,4,5-TES, 3,4-DA, silvex and the like; carbamate herbicides such as IPC, CIPC, swep, barban, BCPC, CEPC, CPPC, and the like; thiocarbamate and dithiocarbamate herbicides such as DCEC, methan sodium, EPTC, diallate, PEBC, perbulate, vernolate and the like; substituted urea herbicides such as norea, siduron, dichloral urea, chloroxuron, cycluron, fenuron, monuron, monuron TCA, diuron, linuron, monolinuron, neburon, buturon, trimeturon and the like; symmetrical triazine, herbicides such as simazine, chlorazine, atraone, desmetryne, norazine, ipazine, prometryn, atrazine, trietazine, simetone, prometone, propazine, ametryne, and the like; chloroacetamide herbicides such as alpha-chloro-N,n-dimethylacetamide, CDEA, CDAA, alpha-chloro-N-isopropylacetamide, 2-chloro-N-isopropylacetanilide, 4-(chloroacetyl)-morpholine, 1-(chloroacetyl)piperidine, and the like; chlorinated aliphatic acid herbicides such as TCA, dalapon, 2,3-dichloropropionic acid, 2,2,3-TPA and the like; chlorinated benzoic acid and phenylacetic acid herbicides such as 2,3,6-TBA, 2,3,5,6-TBA, dicamba, tricamba, amiben, fenac, PBA, 2-methoxy-3,6-dichlorophenylacetic acid, 3-methoxy-2,6-dichlorophenylacetic acid, 2-methoxy-3,4,6-trichlorophenylacetic acid, 2,4-dichloro-3-nitrobenzoic acid and the like; and such compounds as aminotriazole, maleic hydrazide, phenyl mercuric acetate, endothal, biuret, technical chlordane, dimethyl 2,3,5,6-tetrachloroterephthalate, diquat, erbon, DNC, DNBP, dichlobenil, DPA, diphenamid, dipropalin, trifluraline, solan, dicryl, merphos, DMPA, DSMA, MSMA, potassium azide, acrolein, benefin, bensulide, AMS, bromacil, 2-(3,4,-dichlorophenyl)-4-methyl-1,2,4-oxadiazolidine, 3,5-dione, bromoxynil, cacodylic acid, CMA, CPMF, cypromid, DCB, DCPA, dichlone, diphenatril, DMTT, DNAP, EBEP, EXD, HCA, ioxynil, IPX, isocil, potassium cyanate, MAA, MAMA, MCPES, MCPP, MH, molinate, NPA, OCH, paraquat, PCP, picloram, DPA, PCA, pyrichlor, sesone, terbacil, terbutol, TCBA, brominil, CP-50144, H-176-1, H-732, M-2091, planavin, sodium tetraborate, calcium cyanamid, DEF, ethyl xanthogen disulfide, sindone, sindone B, propanil and the like.

Such herbicides can also be used in the methods and composition of this invention in the form of their salts, esters, amides, and other derivatives whenever applicable to the particular patent compounds.

Weeds are undesirable plants growing where they are not wanted, having no economic value, and interfering with the production of cultivated crops, with the growing of ornamental plants, or with the welfare of livestock. Many types of weeds are known, including annuals such as pigweed, lambsquarter, foxtail, crabgrass, wild mustard, field pennycress, ryegrass, goose-grass, chickweed, wild oats, velvet leaf, purselane, barnyard grass, smartweed, knotweed, cocklebur, wild buckwheat, kochia, medic corn cockle, ragweed, sowthistle, coffee-weed, croton, cuphea, dodder, fumitory, groundsel, hemp nettle, knowel, spurge, spurry, emex, jungle rice, pondweed, dog fennel, carpetweed, morning glory, bedstraw, ducksalad and naiad; biennials such as wild carrot, matricaria, wild barley, campion, chamomile, burdock, mullein, roundleaved mallow, bull thistle, hounds-tongue, moth mullein, and purple star thistle; or perennials such as white cockle, perennial ryegrass, quackgrass, Johnson grass, Canada thistle, hedge bindweed, Bermuda grass, sheep sorrel, curly dock, nutgrass, field chickweed, dandelion, campanula, field bindweed, Russian knapweed, mesquite, toadflax, yarrow, aster, gromwell, horsetail, ironweed, sesbania, bulrush, cattail and wintercress.

Similarly, such weeds can be classified as broadleaf or grassy weeds. It is economically desirable to control the growth of such weeds without damaging beneficial plants or livestock.

The new compounds of this invention are particularly valuable for weed control because they are toxic to many species and groups of weeds while they are relatively nontoxic to many beneficial plants. The exact amount of compound required will depend on a variety of factors, including the hardiness of the particular weed species, weather, type of soil, method of application, the kind of beneficial plants in the same area, and the like. Thus, while the application of up to only about one or two ounces of active compound per acre may be sufficient for good control of a light infestation of weeds growing under adverse conditions, the application of ten pounds or more of active compound per acre may be required for good control of a dense infestation of hardy perennial weeds growing under favorable conditions.

The herbicidal toxicity of the new compounds of this invention can be illustrated by many of the established testing techniques known to the art, such as pre- and post-emergence testing.

The herbicidal activity of the compounds of this invention was demonstrated by experiments carried out for the pre-emergence control of a variety of weeds. In these experiments small plastic greenhouse pots filled with dry soil were seeded with the various weed seeds. Twenty-four hours or less after seeding, the pots were sprayed with water until the soil was wet and the test compounds formulated as aqueous emulsions of acetone solutions containing emulsifiers were sprayed at the indicated concentrations on the surface of the soil.

After spraying, the soil containers were placed in the greenhouse and provided with supplementary heat as required and daily or more frequent watering. The plants were maintained under these conditions for a period of from 15 to 21 days, at which time the condition of the plants and the degree of injury to the plants was rated on a scale of from 0 to 10, as follows: 0=no injury, 1,2,=slight injury, 3,4=moderate injury, 5,6=moderately severe injury, 7,8,9=severe injury and 10=death. The effectiveness of these compounds is demonstrated by the following data set out in Tables I and II. Numbers with decimal places are the result of averaging two or more ratings obtained from replicate experiments.

The herbicidal activity of the compounds of this invention was also demonstrated by experiments carried out for the post-emergence control of a variety of weeds. In these experiments the compounds to be tested were formulated as aqueous emulsions and sprayed at the indicated dosage on the foliage of the various weed species that have attained a prescribed size. After spraying, the plants were placed in a greenhouse and watered daily or more frequently. Water was not applied to the foliage of the treated plants. The severity of the injury was determined 10 to 15 days after treatment and was rated on the scale of from 0 to 10 heretofore described. The effectiveness of these compounds is demonstrated by the following data set forth in Tables III and IV. Values with decimal places again are the result of averaging of replicate experiments.

TABLE I

PRODUCT OF EXAMPLE 4
Pre-emergence: Injury Rating
Concentration - lbs/acre

| Weed Species | 8.0 | 2.0 | 1.0 | 0.5 | 0.25 | 0.125 |
|---|---|---|---|---|---|---|
| Yellow Nutsedge | 5 | 0 | 0.0 | — | — | — |
| Wild Oats | 10 | 10 | 6.7 | 5.0 | 2.5 | 1.0 |
| Jimsonweed | 10 | 10 | 10.0 | — | 4.0 | 5.0 |
| Velvetleaf | 10 | 10 | 9.0 | 8.5 | 10.0 | 8.5 |
| Johnsongrass | 9 | 10 | 7.7 | 6.5 | 2.5 | 2.0 |
| Pigweed | 9 | 9 | 7.0 | 3.5 | 1.5 | 1.0 |
| Wild Mustard | 10 | 10 | 10.0 | 10.0 | 10.0 | 4.0 |
| Yellow Foxtail | 10 | 8 | 7.0 | 5.5 | 2.0 | 1.5 |
| Barnyardgrass | 10 | 10 | 9.3 | 10.0 | 7.0 | 0.0 |
| Crabgrass | 9 | 8 | 8.0 | 7.0 | 3.0 | 1.5 |
| Cheatgrass | 10 | 9 | 7.0 | 5.0 | 3.5 | 0.5 |
| Morningglory | 8 | 10 | 8.3 | 7.0 | 4.0 | 4.5 |
| Birdweed | — | — | 10.0 | 5.0 | 3.0 | 1.5 |
| Quackgrass | — | — | 5.5 | 4.5 | 4.0 | 2.5 |
| Sprangletop | — | — | 10.0 | 9.0 | 4.5 | 3.5 |
| Pintobean | — | — | 9.5 | 6.5 | 3.0 | 2.5 |
| Sugarbeet | — | — | 9.0 | 8.5 | 8.0 | 9.5 |
| Wheat | — | — | 9.5 | 8.0 | 7.5 | 2.5 |
| Rice | — | — | 4.0 | 3.5 | 3.0 | 2.0 |
| Soybean | — | — | 6.5 | 4.0 | 1.0 | 1.0 |
| Cotton | — | — | 10.0 | 5.0 | 2.5 | 0.5 |
| Sorghum | — | — | 10.0 | 10.0 | 5.0 | 4.5 |
| Corn | — | — | 7.0 | 5.5 | 3.0 | 0.5 |
| Alfalfa | — | — | 10.0 | 3.5 | 2.0 | 1.0 |
| Oat | — | — | 6.5 | 2.5 | 2.0 | 1.0 |

TABLE II

PRODUCT OF EXAMPLE 7
Pre-emergence: Injury Rating
Concentration - lbs/acre

| Weed Species | 2.0 | 1.0 | 0.5 | 0.25 | 0.125 |
|---|---|---|---|---|---|
| Yellow Nutsedge | 3.0 | 0.0 | 0.0 | — | — |
| Wild Oats | 10.0 | 9.3 | 2.7 | 0.0 | 0.0 |
| Jimsonweed | 10.0 | 4.0 | 2.5 | 4.0 | 1.0 |
| Velvetleaf | 10.0 | 10.0 | 8.5 | 5.5 | 1.0 |
| Johnsongrass | 10.0 | 6.5 | 3.2 | 0.0 | 0.0 |
| Pigweed | 10.0 | 6.0 | 3.5 | 0.0 | 0.0 |
| Wild Mustard | 10.0 | 9.0 | 10.0 | 1.0 | 0.5 |
| Yellow Foxtail | 9.0 | 6.7 | 2.2 | 0.5 | 0.5 |
| Barnyardgrass | 10.0 | 5.7 | 5.2 | 2.0 | 1.0 |
| Crabgrass | 6.0 | 4.5 | 1.7 | 1.5 | 2.0 |
| Cheatgrass | 10.0 | 6.7 | 1.7 | 0.5 | 0.0 |
| Morningglory | 10.0 | 7.6 | 8.4 | 5.0 | 1.5 |
| Birdweed | — | 10.0 | 5.5 | 3.0 | 0.0 |
| Cocklebur | 7.0 | 2.0 | 1.0 | 0.0 | — |

TABLE II-continued

PRODUCT OF EXAMPLE 7
Pre-emergence: Injury Rating
Concentration - lbs/acre

| Weed Species | 2.0 | 1.0 | 0.5 | 0.25 | 0.125 |
|---|---|---|---|---|---|
| Quackgrass | — | 10.0 | 6.0 | 2.5 | 0.0 |
| Sprangletop | — | 5.0 | 2.5 | 0.0 | 0.0 |
| Pintobeau | — | 6.0 | 3.0 | 0.0 | 0.0 |
| Sugarbeet | — | 10.0 | 10.0 | 8.0 | 6.0 |
| Wheat | — | 9.5 | 5.5 | 1.5 | 1.0 |
| Rice | — | 4.0 | 2.5 | 3.5 | 0.0 |
| Soybean | 6.0 | 3.7 | 0.7 | 0.3 | 1.0 |
| Cotton | 2.0 | 1.7 | 0.0 | 0.0 | 0.0 |
| Sorghum | — | 10.0 | 4.0 | 2.0 | 1.0 |
| Corn | — | 3.0 | 0.5 | 0.0 | 0.0 |
| Alfalfa | — | 5.0 | 0.0 | 0.0 | 0.0 |
| Oat | — | 4.0 | 0.0 | 0.0 | 0.0 |

TABLE III

PRODUCT OF EXAMPLE 4
Post-emergence: Injury Rating
Concentration - lbs/acre

| Weed Species | 2.0 | 1.0 | 0.5 | 0.25 | 0.125 |
|---|---|---|---|---|---|
| Wild Mustard | 10.0 | 10.0 | 10.0 | 10.0 | 10.0 |
| Wild Oat | 10.0 | 3.5 | 4.0 | 2.0 | 1.0 |
| Bindweed | 10.0 | 10.0 | 10.0 | 10.0 | 3.0 |
| Barnyardgrass | 10.0 | 10.0 | 10.0 | 10.0 | 5.0 |
| Crabgrass | 9.0 | 9.5 | 9.5 | 10.0 | 10.0 |
| Yellow Foxtail | 9.0 | 10.0 | 10.0 | 6.0 | 4.0 |
| Johnsongrass | 10.0 | 9.5 | 8.0 | 3.0 | 2.0 |
| Morningglory | 10.0 | 10.0 | 10.0 | 10.0 | 10.0 |
| Jimsonweed | 10.0 | 10.0 | 10.0 | 10.0 | 5.0 |
| Yellow Nutsedge | 5.0 | 2.0 | 2.0 | — | — |
| Pigweed | 10.0 | 10.0 | 10.0 | 10.0 | 10.0 |
| Velvetleaf | — | 10.0 | 10.0 | 10.0 | 10.0 |
| Quackgrass | — | 10.0 | 6.0 | 4.0 | 2.0 |
| Sprangletop | — | 10.0 | 10.0 | 4.0 | 3.0 |
| Cheatgrass | — | 10.0 | 10.0 | 2.0 | 2.0 |
| Pintobeau | — | 10.0 | 10.0 | 10.0 | 10.0 |
| Sorghum | — | 10.0 | 10.0 | 10.0 | 10.0 |
| Wheat | — | 10.0 | 5.0 | 10.0 | 1.0 |
| Rice | — | 5.0 | 4.0 | 4.0 | 2.0 |
| Cotton | — | 10.0 | 10.0 | 10.0 | 10.0 |
| Corn | — | 7.0 | 10.0 | 4.0 | 3.0 |
| Alfalfa | — | 10.0 | 10.0 | 10.0 | 10.0 |
| Oat | — | 2.0 | 2.0 | 0.0 | 0.0 |
| Soybean | — | 10.0 | 10.0 | 10.0 | 10.0 |
| Sugarbeet | — | 10.0 | 10.0 | 10.0 | 10.0 |

TABLE IV

PRODUCT OF EXAMPLE 7
Post-emergence: Injury Rating
Concentration - lbs/acre

| Weed Species | 2.0 | 1.0 | 0.5 | 0.25 | 0.125 | 0.062 |
|---|---|---|---|---|---|---|
| Wild Mustard | 10.0 | 10.0 | 10.0 | 10.0 | 6.5 | 2.0 |
| Wild Oat | 10.0 | 5.0 | 2.0 | 0.0 | 0.0 | 0.0 |
| Bindweed | 10.0 | 10.0 | 9.0 | 5.5 | 1.0 | 0.0 |
| Barnyardgrass | 10.0 | 10.0 | 7.2 | 6.0 | 3.5 | 2.0 |
| Crabgrass | 10.0 | 8.7 | 6.2 | 4.5 | 2.0 | 0.0 |
| Yellow Foxtail | 10.0 | 5.7 | 5.7 | 2.5 | 1.0 | 0.0 |
| Johnsongrass | 10.0 | 8.0 | 6.0 | 5.5 | 3.5 | 5.0 |
| Morningglory | 10.0 | 10.0 | 10.0 | 6.5 | 10.0 | 5.0 |
| Jimsonweed | 10.0 | 9.3 | 9.2 | 8.5 | 8.5 | 10.0 |
| Yellow Nutsedge | 2.0 | 0.5 | 0.0 | — | — | — |
| Pigweed | 10.0 | 8.3 | 7.5 | 6.0 | 4.0 | 3.0 |
| Velvetleaf | — | 10.0 | 10.0 | 10.0 | 8.5 | 7.0 |
| Quackgrass | — | 10.0 | 10.0 | 7.0 | 2.0 | 2.0 |
| Sprangletop | — | 10.0 | 6.0 | 5.5 | 1.0 | 0.0 |
| Cheatgrass | — | 10.0 | 5.0 | 5.0 | 0.0 | 0.0 |
| Pintobeau | — | 5.0 | 10.0 | 7.0 | 7.0 | 3.0 |
| Sorghum | — | 10.0 | 5.0 | 1.0 | 1.0 | 0.0 |
| Wheat | — | 2.0 | 1.5 | 1.0 | 0.0 | 0.0 |
| Rice | — | 7.0 | 5.5 | 10.0 | 0.5 | 0.0 |
| Cotton | — | 10.0 | 10.0 | 8.5 | 7.5 | 10.0 |
| Corn | — | 4.0 | 3.0 | 0.5 | 0.5 | 0.0 |
| Alfalfa | — | 10.0 | 10.0 | 9.5 | 9.5 | 4.0 |
| Oat | — | 2.0 | 0.5 | 1.0 | 0.5 | 0.0 |
| Soybean | 10.0 | 10.0 | 7.0 | 4.5 | 3.5 | 3.0 |
| Sugarbeet | — | 10.0 | 10.0 | 8.5 | 6.5 | 2.0 |

I claim:
1. A compound of the formula

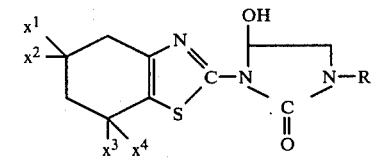

wherein each $x^1$, $x^2$, $x^3$ and $x^4$ is selected from the group consisting of alkyl, halogen and cyano; and R is selected from the group consisting of alkyl, alkenyl and haloalkyl.

2. The compound of claim 1, 1-(5,5,7,7-tetramethyl-4,5,6,7-tetrahydrobenzothiazol-2-yl)-3-methyl-5-hydroxy-1,3-imidazolidin-2-one.

3. The compound of claim 1, 1-(5,5,7-trimethyl-7-cyano-4,5,6,7-tetrahydrobenzothiazol-2-yl)-3-methyl-5-hydroxy-1,3-imidazolidin-2-one.

4. A herbicidal composition comprising an inert carrier and, an essential active ingredient, in a quantity toxic to weed, a compound of claim 1.

5. A method of controlling weeds which comprises contacting said weed with a herbicidal composition comprising an inert carrier and, as an essential active ingredient, in a quantity toxic to weeds, a compound of claim 1.

* * * * *